United States Patent
Lin

(10) Patent No.: US 6,911,009 B2
(45) Date of Patent: Jun. 28, 2005

(54) SPHYGMOGRAM MEASURE METHOD AND DEVICE FOR TWO CLOSED MEASURED POINTS

(75) Inventor: Chin-Yuh Lin, Taichung (TW)

(73) Assignee: E-Med Biotech Inc., Taichung (TW)

( * ) Notice: Subject to any disclaimer, the term of this patent is extended or adjusted under 35 U.S.C. 154(b) by 44 days.

(21) Appl. No.: 10/421,744

(22) Filed: Apr. 24, 2003

(65) Prior Publication Data

US 2003/0204143 A1 Oct. 30, 2003

(30) Foreign Application Priority Data

Apr. 26, 2002 (TW) ........................................ 91108622 A

(51) Int. Cl.⁷ .............................................. A61B 5/02
(52) U.S. Cl. ...................................... 600/485; 600/300
(58) Field of Search ................................. 600/485–507

(56) References Cited

U.S. PATENT DOCUMENTS

| | | | | |
|---|---|---|---|---|
| 4,245,648 A | * | 1/1981 | Trimmer et al. | 600/493 |
| 4,263,918 A | * | 4/1981 | Swearingen et al. | 600/494 |
| 4,993,422 A | * | 2/1991 | Hon et al. | 600/485 |
| 5,301,675 A | * | 4/1994 | Tomita | 600/485 |
| 5,564,427 A | * | 10/1996 | Aso et al. | 600/494 |
| 5,941,828 A | * | 8/1999 | Archibald et al. | 600/494 |
| 6,210,340 B1 | * | 4/2001 | Amano et al. | 600/500 |
| 6,730,040 B2 | * | 5/2004 | Lee et al. | 600/485 |

FOREIGN PATENT DOCUMENTS

JP 05261074 * 10/1993 .............. A61B/5/02

* cited by examiner

*Primary Examiner*—Robert L. Nasser
*Assistant Examiner*—Patricia C. Mallari
(74) *Attorney, Agent, or Firm*—Rosenberg, Klein & Lee

(57) ABSTRACT

A sphygmogram measure method and device includes an upstream and a downstream pressure sensor arranged in accordance with the bloodstream direction to measure the pulse pressure of two adjacent points on radial artery in the wrist. The pulse pressures are processed and converted to analog signals by an amplitude filter circuit and an adjusting circuit. The analog signal of upstream pulse pressure is converted to a digital signal, which is stored in a digital signal process unit. The signals of upstream pulse pressure and downstream pulse pressure are also transmitted as a start signal and a stop signal respectively to a counter which measures the time lag of a pulse wave passing through the two pressure sensors. The digital signal process unit uses the digital signals of upstream pulse pressure and time lag to calculate the digital signal of downstream pulse pressure.

6 Claims, 3 Drawing Sheets

SPHYGMOGRAM MEASURE METHOD AND DEVICE FOR TWO CLOSED MEASURED POINTS

BACKGROUND OF THE INVENTION

1. Field of the Invention

This invention relates to a sphygmogram measure method and device, which allows a user to determine pulse pressure at two adjacent points.

2. Description of Prior Art

Conventional methods of sphygmogram rely on measuring the pressure of the pulse and the variation of the waveform, or changing the pressure into spectrums for analysis, to evaluate the health status of a person. In addition, Doppler ultrasound to measure blood flow, and measuring the velocity of red blood cell using infrared were also used. However, these methods would only obtain single data at one time period, instead of multiple signals simultaneously. Single data of pulse pressure, blood flow, or flow rate was insufficient for expressing all aspects of cardiovascular status, because the same pulse pressure may yield different blood flow due to different diameter or compliance of vessel. Furthermore, the health status and hemokinetics are closely related that the changes cannot be accurately understood by single data of pulse pressure, flow rate or flow velocity.

Suppose that the bloodstream is a laminar flow and the vessel is a linear resilient tube, a formula of blood flow rate is as follow:

$$Q = \frac{\pi}{20\alpha L \mu}\left[\left(a_0 + \frac{\alpha P_0(t)}{2}\right)^5 - \left(a_0 + \frac{\alpha P_L(t)}{2}\right)^5\right]$$

Wherein:

Q is the blood flow rate;

$$\alpha = \frac{\Delta a}{p}$$

is the vessel compliance $\Delta a$ is the variation of the vessel diameter and p is the pulse pressure value;

L is the distance between two measure points;

$\mu$ is the blood viscosity coefficient;

$a_0$ is the unstressed vessel diameter; and $P_0(t)$ and $P_L(t)$ are the pulse pressure values of two measure points.

Therefore, the values of the vessel compliance $\alpha$, the blood viscosity coefficient $\mu$, the vessel diameter $a_0$, the pulse pressure values of the two measure points $P_0(t)$ and $P_L(t)$, and the distance between the two measure points L are essential to calculate the blood flow rate from the above formula. Conventional measure methods and devices are unable to provide simultaneously all the above data in a single process by the same device.

Theoretically, to obtain the blood flow rate in accordance with above formula, the shorter the distance between two measure points is, the more accurate the estimate of blood flow rate can be. But it will be more difficult to measure pulse pressures of two measure points when the distance is closed. According to traditional Chinese medicine, the two measure points must be within one fingertip, that is, the distance between the two measure points will be appropriate between 2 to 3 mm. Refer to FIG. 1, the pulse wave velocity (PWV) in human radial artery at wrist is about 3.5 to 4.5 m/sec, which the pulse takes approximately 0.5 millisecond to pass through these two points; and most of current-in-used sphygmorgrah devices sample the pulse pressure by frequencies from 200 to 400 Hz, i.e. a period from 20 to 50 millisecond, which obviously indicates that these devices are not able to distinguish the difference of pulse pressures at these closed points.

Besides, the difference of pulse pressure between two adjacent points is rather small, it makes difficult to convert pulse pressures from analog signal into digital signal with satisfied resolutions.

Another important factor affecting the outcome of calculation for blood flow rate is vessel compliance $\alpha$. A research on carotid artery shows that practical vessel compliance is non-linear which varies during arterial systole and diastole. It means that the above formula should be modified, because the vessel compliance $\alpha$ is no longer a constant value.

Based upon the definition of the vessel compliance, the ratio of the variation of vessel's diameter to the pulse pressure, or the slope of a variation of vessel's diameter and pulse pressure curve at measure point, intuitionally, it seems simply install a pressure sensor and a displacement sensor at measure point to acquire the pulse pressure signal and the variation of vessel's diameter signal and then to calculate the nonlinear vessel compliance in a digital processing unit. But in reality, it is not applicable for noninvasive solution: at measure point, a pressure sensor should be holding stationary at certain depth against the vessel to have pressure signals and a displacement sensor should be placed to sense the variations of the vessel's diameter. A stationary pressure sensor and a movable displacement sensor cannot be connected together to have both pressure and variations of vessel's diameter at same measure point which results in failure of computing nonlinear vessel compliance.

As mentioned above, the conventional methods and devices can acquire neither the values of two pulse pressures $P_0(t)$ and $P_L(t)$, nor the vessel compliance $\alpha$.

Accordingly, there is a need for an improved sphygmogram measure method and device, which provide solutions to the disadvantages of current counterparts.

SUMMARY OF THE INVENTION

It is therefore the objective of the present invention to provide a sphygmogram measure method and device, which measure the pulse pressure at two adjacent measure points, with the steps of:

A. Positioning an upstream pressure sensor and a downstream pressure sensor being arranged at a certain distance in accordance with the bloodstream direction;

B. Acquiring the signals from upstream and downstream pressure sensors and through its signal conditioner to have the analogy form of upstream pressure $P_0(t)$ and downstream pressure $P_L(t)$, wherein the function of the signal conditioner is to amplify signals, filter out noise, adjust the signal level, compensate the drift, etc.;

C. Converting the analogy form of upstream pressure $P_0(t)$ into a digital upstream pressure $P_0(n)$ by A/D converter that the sampling frequency is 200 to 400 Hz, storing the digital upstream pressure into the digital signal process unit;

D. Delivering the analog signals of upstream and downstream pressures $P_0(t)$ and $P_L(t)$ to a low-pass circuit to obtain the fundamental wave of the pulse pressure, then using a cross-zero detector, a peak detector to trigger or a stop counter circuit which in turn detects the time lag $\tau$ and the time lag $\tau$ is stored in a digital process unit; and E. Calculating the digital downstream pressure $P_L(n)$ in the digital signal process unit by using upstream pressure $P_0(n)$ and time lag $\tau$, wherein $P_L(n) \approx P_0(n+\tau)$.

Further benefits and advantages of the present invention will appear from the following description, taken together with the accompanying drawings.

DETAILED DESCRIPTION OF THE INVENTION

Figure 1:
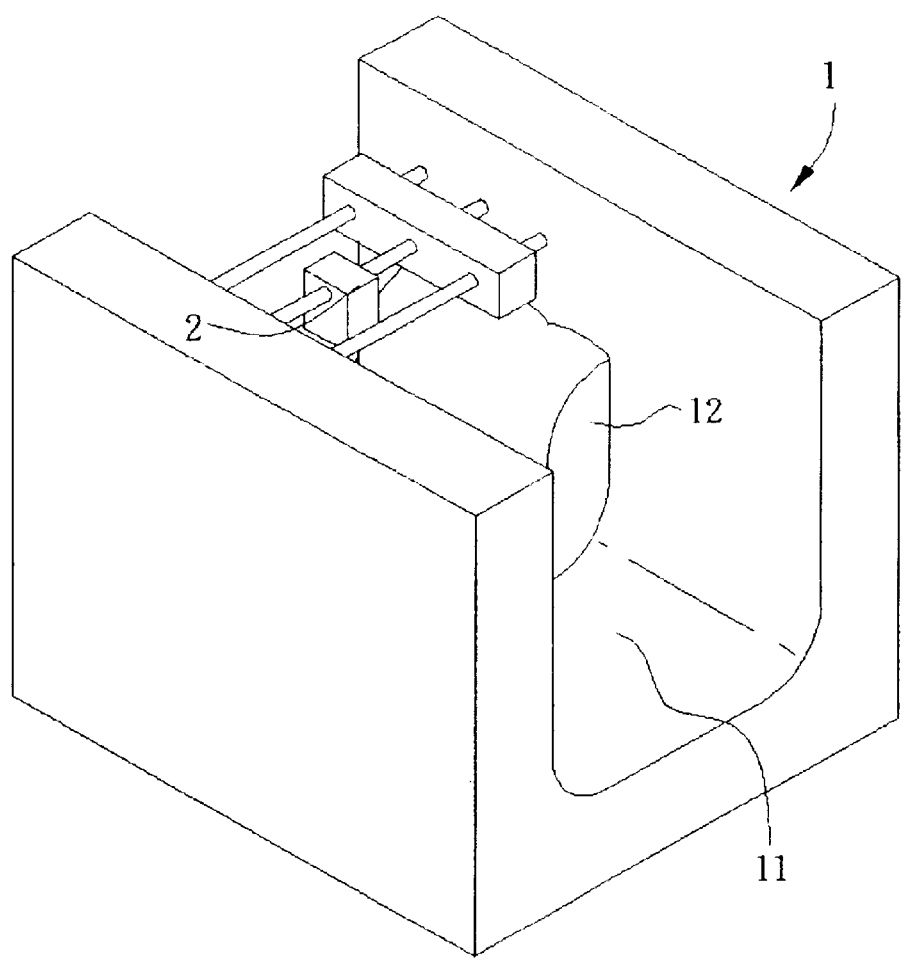
FIG. 1 is a perspective view of a sphygmogram measure device in accordance with the present invention.

FIG. 1 shows a noninvasive sphygmogram measure device in accordance with the present invention. This embodiment comprises a wrist holder (1), a set of pressure-sensing device (2), a detecting circuit (3), and a digital signal process unit (not shown).

The wrist holder (1) includes a receiving space (11) longitudinally defined in the wrist holder (1). The receiving space (11) is adapted to place an examinee's wrist with the side of radial artery therein upward. Two bladders (12) secure the wrist respectively on the two sidewalls of receiving space (11), and function to stabilize the wrist (but not press over the radial artery) when filled with air gradually.

Figure 2:
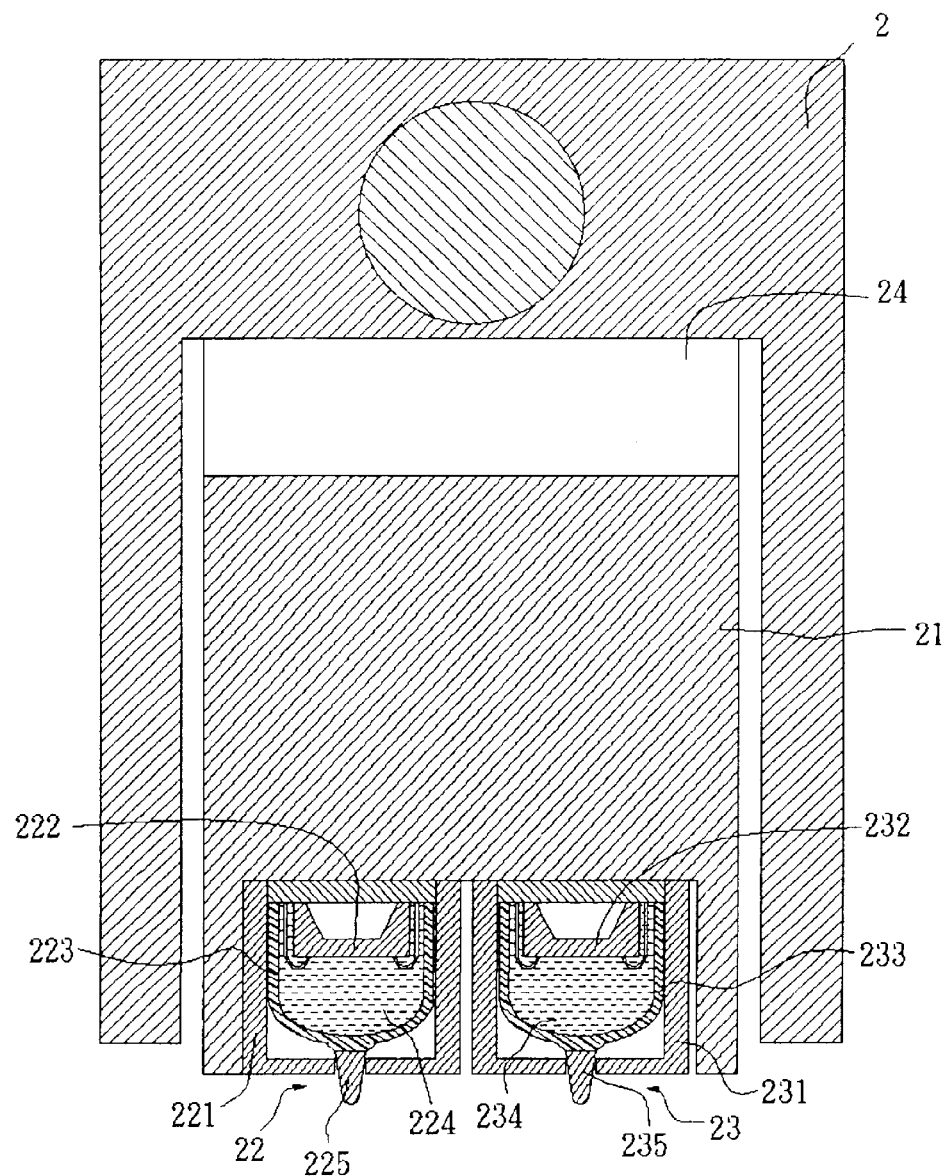
FIG. 2 is a side plan view of a pressure sense device of the sphygmogram measure device shown in FIG. 1.

Referring to FIG. 1 and FIG. 2, a set of pressure-sensing device (2) is installed in the wrist holder (1) above the two bladders (12). The pressure-sensing device (2) includes a seat (21) to allow placing a wrist under examination, and a driving device (24) is disposed to downward press the seat (21). An upstream pressure sensor (22) and a downstream pressure sensor (23) are mounted respectively on the bottom side of the seat (21). The distance between the centers of upstream pressure sensor (22) and downstream pressure sensor (23) is about 2 to 3 millimeters.

The upstream pressure sensor (22) comprises a first casing (221) mounted in the seat (21), an upstream micro-pressure sensor (222) mounted in the first casino (221) and a first resilient cover (223) covering the upstream micro-pressure sensor (222). The downstream pressure sensor (23) also includes a second casing (231) mounted in the seat (21), a downstream micro-pressure sensor (232) mounted in the second casing (231) and a second resilient cover (233) covering the downstream micro-pressure sensor (232) in the pressure-sensing device (2).

A first chamber (224) is defined between the upstream micro-pressure sensor (222) and the first resilient cover (223), and fills with silicon oil. A second chamber (234) is defined between the downstream micro-pressure sensor (232) and the second resilient cover (233), and fills with silicon oil. A first column head (225) on the central tip of the first resilient cover (223) extends from the bottom edge of the first casing (221) about 0.25 mm, and a second column head (235) on the tip of the second resilient cover (233) stand out the bottom edge of the second casing (231) as well. The contact tips of the first column head (225) and the second column head (235) must be narrower than a diameter of the measured vessel so as to receive fully the pulse pressures at the measured points.

The column heads (225,235) are made of hard material, which can endure pressure and prevent the column head from deformity. When the pulse presses the column heads (225,235) then transmits through the silicon oil in both chambers (224,234) to the upstream micro-pressure sensor (222) and the downstream micro-pressure sensor (232) respectively.

Figure 3:
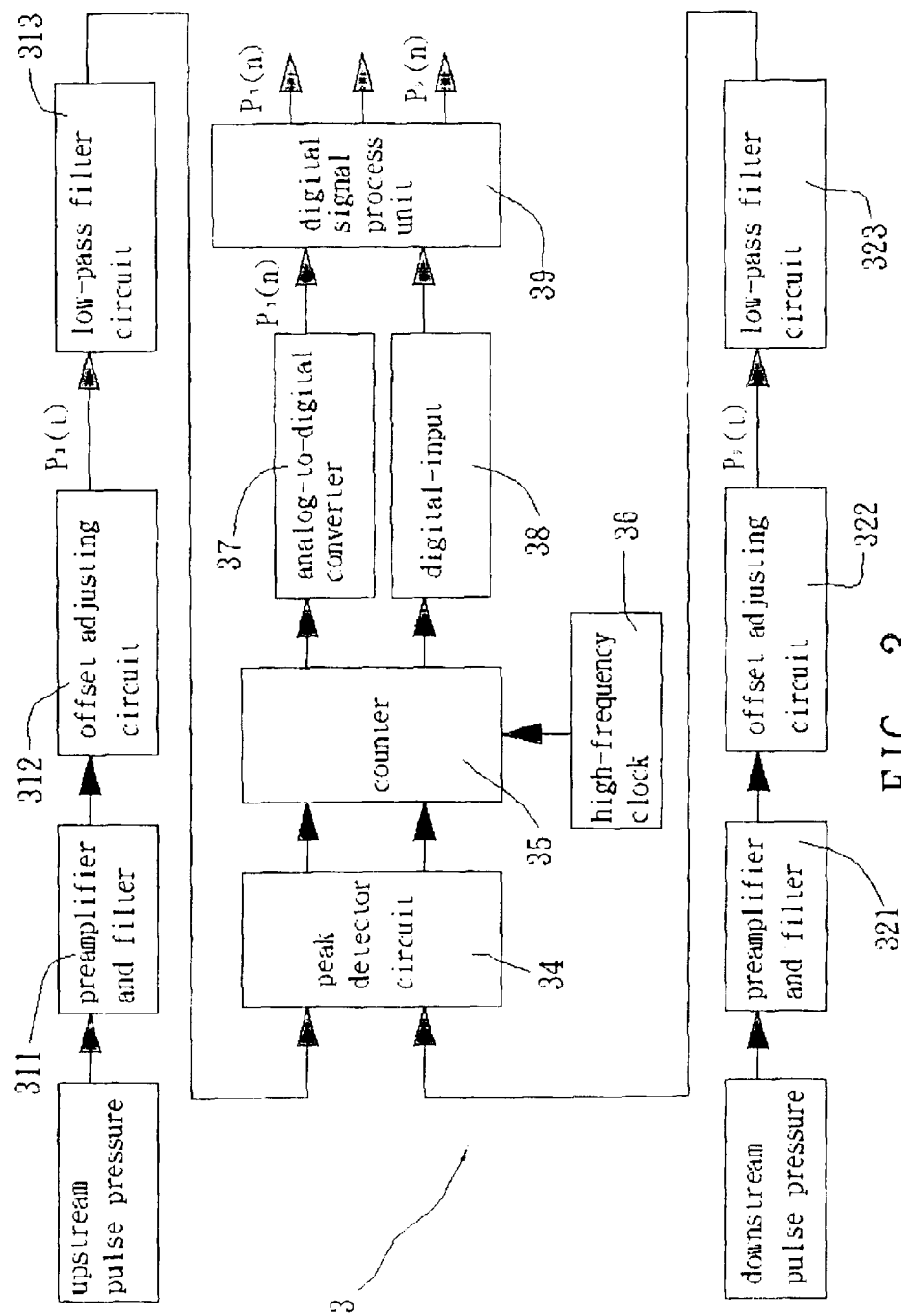
FIG. 3 is a flow chart showing how the sphygmogram device of the present invention obtains a variety of data.

FIG. 3 is a functional diagram of a detecting circuit (3), which shows the measurement of the pulse pressure at adjacent closed points. In the detecting circuit (3), a preamplifier and a filter circuits (311, 321) and two offset adjusting circuits (312, 322) condition the signals from the upstream pressure sensor (22) and the downstream pressure sensor (23) respectively, two low-pass filter circuits (313, 323) show the fundamental wave of the pulse pressures for easily level detecting, a zero-cross detector, or a peak detector circuit (34) trigger or stop the counts of the following counter (35). A 10 MHz high-frequency clock (36) provides the resolution of the counter. An analog-to-digital converter (37) and a digital-input (38) are the interface to the digital signal process unit (39).

The measurement of the pulse pressures at two adjacent closed points are described as follows.

A. Placing an examinee's wrist with the sides of radial artery therein upward in the wrist holder (1);

B. Moving down the column heads (225, 235) against the vessel to acquire the upstream pressure $P_0(t)$ and downstream pressure $P_L(t)$;

C. Filter out the upstream pressure $P_0(t)$ and downstream pressure $P_L(t)$ by low-pass filters (313,323) to acquire the fundamental waves;

D. Detecting the zero-cross signal of the fundamental wave of the upstream and downstream pressure signals to trigger and stop the counts of the following counter, and obtain the time lag $\tau$ between these two pressures by output of the counter;

E. Converting the analogy form of upstream pressure $P_0(t)$ into a digital upstream pressure $P_0(n)$ by A.D converter that the sampling frequency is 200 to 400 Hz;

F. Storing the digital downstream pressure $P_0(n)$ and $\tau$ in the digital signal process unit; and H. Calculate the digital downstream pressure $P_L(n)$ in digital signal process unit by using upstream pressure $P_0(n)$ and time lag $\tau$, where $P_L(n)\ P_0(n+\tau)$.

Although the invention has been described by means of preferred embodiments, numerous possible modifications and variations could be made thereto by those skilled in the art without departing from the scope of the invention set forth in the claims.

What is claimed is:

1. A sphygmogram measure method for measuring pulse pressure at two adjacent measure points, comprising the steps of:

Step 1: positioning an upstream pressure sensor and a downstream pressure sensor at a certain distance L in accordance with the bloodstream direction;

Step 2: acquiring the signals from the upstream and the downstream pressure sensors and passing the signals through preamplifier and filter circuits and offset adjust circuits to acquire an analog form of upstream pressure $P_0(t)$ and downstream pressure $P_L(t)$;

Step 3: converting the analogy analog form of upstream pressure $P_0(t)$ into a digital upstream pressure $P_0(n)$ using an A/D converter at a sampling frequency of 200 to 400 Hz and then storing the digital upstream pressure into a digital signal process unit;

Step 4: filtering the analog form of upstream pressure $P_0(t)$ and downstream pressure $P_L(t)$ by two low-pass filters to obtain their fundamental waves;

Step 5: detecting the zero-cross signal of the fundamental wave of the upstream and downstream pressure signals to trigger and stop the counting of a counter, and obtaining the time lag $\tau$ between the two pressure signals by output of the counter;

Step 6: storing the digitized upstream pressure signal $P_O(t)$ and time lag $\tau$ in the digital signal process unit; and Step 7: calculating the digital downstream pressure $P_L(n)$ in the digital signal process unit by using the digital upstream pressure $P_O(n)$ and time lag $\tau$, where $P_L(n)$ $P_O(n+\tau)$.

2. The sphygmogram measure method as claimed in claim 1, wherein the distance between the upstream pressure sensor and the downstream pressure sensor is 2 to 3 millimeters.

3. A sphygmogram measure device for measuring pulse pressure at two adjacent measure points, comprising:

a wrist holder that stabilizes a wrist but does not press a vessel therein;

a set of pressure sensing devices mounted in the wrist holder and comprising a seat, an upstream pressure sensor mounted in the seat, a downstream pressure sensor mounted in the seat and a drive device disposing the seat downwards, the upstream pressure sensor including a first casing mounted in the seat, an upstream chip mounted in the first casing and a first resilient cover covering the upstream chip, the downstream pressure sensor including a second casing mounted in the seat, a downstream chip mounted in the second casing and a second resilient cover covering the downstream chip, a first chamber defined between the upstream chip and the first resilient cover and a second chamber defined between the downstream chip and the second resilient cover, the first and the second chambers filled with fluid, the central tip of the first resilient cover being a first column head which extends out of the bottom edge of first casing and the central tip of second resilient cover being a second column head extending out of the bottom edge of second casing ; and a detecting circuit connected to the upstream pressure sensor and the downstream pressure sensor.

4. The sphygmogram measure device in claim 3, wherein the contact tips of first column head and second column head must be narrower than the diameter of the measured vessel, and the distance between the upstream pressure sensor and the downstream pressure sensor is about 2 to 3 millimeters.

5. The sphygmogram measure device in claim 3, wherein the detecting circuit comprises:

a first preamplifier filter circuit connected to the upstream pressure sensor and a second preamplifier and filter circuit connected to the downstream pressure sensor;

two offset adjusting circuits connected to the first and second preamplifier and filter circuit respectively;

two low-pass filter circuits connected to the two adjusting circuits respectively;

a peak detector circuit connected to the two low-pass filter circuits, and a counter connected to the peak detector circuit;

a high frequency clock connected to the counter;

an analog-to-digital converter connected to the offset adjusting circuit and the low-pass filter circuit of the upstream pressure sensor; and an input/output interfacing a digital signal process unit and the analog-to-digital converter or a digital input device.

6. The sphygmogram measure device in claim 3, wherein the upstream pressure sensor and the downstream pressure sensor are positioned a distance L in accordance with a blood stream direction and the signals from upstream and downstream pressure sensors are acquired and passed through preamplifier and filter circuits and offset adjust circuits to obtain an analog form of upstream pressure $P_O(t)$ and downstream pressure $P_L(t)$, the detecting circuit processes data with the steps of:

Step 1: converting the analog form of upstream pressure $P_O(t)$ into a digital upstream pressure $P_O(n)$ by using an A/D converter at a sampling frequency of 200 to 400 Hz and then storing the digital upstream pressure $P_O(n)$ into a digital signal process unit;

Step 2: filtering out the analog form of the upstream pressure $P_O(t)$ and the downstream pressure $P_L(t)$ by two low-pass filters to obtain their fundamental waves;

Step 3: detecting the zero-cross signal of the fundamental wave of the upstream and downstream pressure signals to trigger and stop the counting of a counter, and obtaining the time lag $\tau$ between the two pressure signals by an output of the counter;

Step 4: storing the digitized upstream pressure signal $P_O(n)$ and time lag $\tau$ in the digital signal process unit; and Step 5: calculating the digital downstream pressure $P_L(n)$ in the digital signal process unit by using the digitized upstream pressure $P_O(n)$ and time lag $\tau$, where $P_L(n)$ $P_O(n+\tau)$.

* * * * *